United States Patent [19]

Müller et al.

[11] 4,383,948
[45] May 17, 1983

[54] HYDRAZONE DERIVATIVES CONTAINING A QUATERNARY AMMONIUM GROUP USEFUL AS UV ABSORBERS

[75] Inventors: Beat Müller; Martin Roth, both of Marly, Switzerland

[73] Assignee: Ciba-Geigy AG, Basel, Switzerland

[21] Appl. No.: 264,929

[22] Filed: May 18, 1981

[30] Foreign Application Priority Data

May 21, 1980 [CH] Switzerland .................. 3962/80

[51] Int. Cl.$^3$ .................. C07C 119/10; G03C 1/70
[52] U.S. Cl. .................. 260/459 A; 260/465 D; 260/465 E; 560/34; 564/251; 564/150; 564/149; 430/72; 430/73
[58] Field of Search .......... 260/459 A, 465 D, 465 E; 560/34; 564/251, 150, 149

[56] References Cited

U.S. PATENT DOCUMENTS 2,818,367 12/1957 Jaworski et al. .................. 564/251
4,150,987 4/1979 Anderson et al. .................. 564/251

FOREIGN PATENT DOCUMENTS 1568725 4/1970 Fed. Rep. of Germany .

Primary Examiner—Nicky Chan
Attorney, Agent, or Firm—Joseph G. Kolodny

[57] ABSTRACT

Hydrazone derivatives of the formula

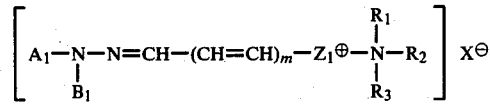

in which $A_1$ is an aromatic radical, $B_1$ is hydrogen, alkyl, cycloalkyl, aralkyl or aryl, $R_1$, $R_2$ and $R_3$ independently of one another are alkyl, cycloalkyl, aralkyl or polyoxyalkylene, $Z_1$ is arylene, $X^\ominus$ is an anion and m is 0, 1, 2 or 3.

The hydrazone derivatives are suitable as UV absorbers, especially in polymer coatings.

7 Claims, No Drawings

HYDRAZONE DERIVATIVES CONTAINING A QUATERNARY AMMONIUM GROUP USEFUL AS UV ABSORBERS

The present invention relates to novel hydrazone derivatives, optionally their vinylogues, processes for their preparation and their use as UV absorbers.

More particularly, the present invention relates to hydrazone derivatives of the formula

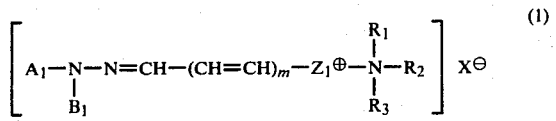

in which $A_1$ is a substituted or unsubstituted aromatic radical, $B_1$ is hydrogen, substituted or unsubstituted alkyl having 1 to 8 carbon atoms, substituted or unsubstituted cycloalkyl having 5 or 6 carbon atoms, substituted or unsubstituted aralkyl having 1 to 4 carbon atoms in the alkyl moiety or substituted or unsubstituted aryl, $R_1$, $R_2$ and $R_3$ independently of one another are substituted or unsubstituted alkyl having in each case 1 to 8 carbon atoms, substituted or unsubstituted cycloalkyl having 5 or 6 carbon atoms, substituted or unsubstituted aralkyl having 1 to 4 carbon atoms in the alkyl moiety or polyoxyalkylene, $Z_1$ is substituted or unsubstituted arylene, $X^\ominus$ is an anion and m is 0, 1, 2 or 3.

The present invention also relates to processes for the preparation of the hydrazone derivatives of the formula (1).

The invention furthermore relates to the use of the compounds according to the invention as UV absorbers, in particular in polymer coatings.

The substituent $A_1$ is an aromatic radical, for example phenyl or naphthyl. $A_1$ is preferably phenyl. Substituents for $A_1$ can be alkyl or alkoxy having in each case 1 to 4, in particular 1 or 2, carbon atoms, hydroxyl or halogen. Preferred halogens are chlorine and bromine. Chlorine is particularly suitable. The aromatic radical can contain 1 or 2 substituents.

Substituent $B_1$ is alkyl having 1 to 8 carbon atoms. The alkyl radicals can be straight-chain or branched. Examples of alkyl radicals are: methyl, ethyl, propyl, i-propyl, butyl, i-butyl, tert.-butyl, amyl, tert.-amyl, 1,1,3,3-tetramethylbutyl, 1methylethylpentyl, hexyl, 1-methylpentyl, neopentyl, 1- or 2-methylhexyl, heptyl, n-octyl, tert.-octyl and 2-ethylhexyl. Alkyl radicals having 1 to 4, in particular 1 or 2, carbon atoms are particularly suitable. Substituents on the alkyl radicals are methoxy, hydroxyl, cyano, halogen, carbalkoxy having 1 to 8, in particular 1 to 4, carbon atoms or carboxamido. Hydroxyl, cyano and carbomethoxy are preferred. Preferred halogens are fluorine, chlorine and bromine, and chlorine is particularly preferred.

In a cycloalkyl radical $b_1$, the ring system comprises 5, but preferably 6, carbon atoms. The ring system can be substituted by alkyl or alkoxy having in each case 1 or 2 carbon atoms, in particular by methyl or methoxy.

An aralkyl radical $B_1$ has 1 to 4, in particular 1 or 2, carbon atoms in the alkyl moiety. The aryl moiety is phenyl or naphthyl. Phenyl is particularly suitable. The aryl moiety can be substituted by alkyl or alkoxy having in each case 1 to 4, in particular 1 or 2, carbon atoms.

An aryl radical $B_1$ is, for example, phenyl or naphthyl, and phenyl is preferred. The phenyl ring can be substituted by alkoxy having 1 to 4, in particular 1 or 2, carbon atoms.

The radicals $R_1$, $R_2$ and $R_3$ independently of one another are alkyl having in each case 1 to 8 carbon atoms. These alkyl radicals can be those mentioned for $B_1$. Alkyl radicals having 1 to 4, in particular 1 or 2, carbon atoms are preferred. They can be substituted by methoxy, hydroxyl, cyano, halogen or carboxamido. The hydroxyl radical is especially preferred. Suitable halogens are fluorine, chlorine and bromine. Chlorine is a particularly valuable halogen.

A cycloalkyl radical $R_1$, $R_2$ or $R_3$ is preferably a ring with 5 or 6 carbon atoms. Cyclohexyl is the preferred ring system. Substituents for the cycloalkyl radical are methyl and methoxy.

An aralkyl radical $R_1$, $R_2$ or $R_3$ has 1 to 4, in particular 1 or 2, carbon atoms in the alkyl moiety. The aryl moiety is preferably phenyl, which can be further substituted by alkyl or alkoxy having in each case 1 to 4, in particular 1 or 2, carbon atoms. Benzyl is a particularly suitable aralkyl radical.

A (poly)oxyalkylene radical $R_1$, $R_2$ or $R_3$ is preferably $H\text{-}(OC_2H_4)_{\overline{n}1}$, in which $n_1$ is 1, 2 or 3. $H\text{-}(OC_2H_4)_{\overline{n}2}$ in which $n_2$ is 1 or 2 is particularly suitable.

$Z_1$ is arylene, for example phenylene or naphthylene, and phenylene is particularly suitable. This arylene radical can be substituted by hydroxyl, cyano, nitro, halogen or alkyl or alkoxy having in each case 1 to 4 carbon atoms. Preferred substituents are methoxy, hydroxyl and chlorine. The phenyl ring can carry 1 or 2 of the substituents.

$X^\ominus$ is an anion of a monobasic or polybasic mineral acid, for example sulfate, chloride, bromide, iodide or methyl-sulfate, and m is 0, 1, 2 or 3, preferably 0 or 1.

Particularly suitable compounds of the formula (1) are those of the formula

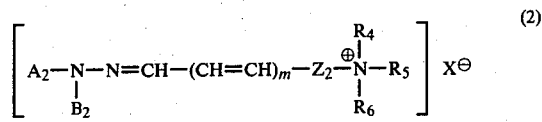

in which $A_2$ is substituted or unsubstituted phenyl, $B_2$ is hydrogen, alkyl which has 1 to 8 carbon atoms and is unsubstituted or substituted by methoxy, hydroxyl, cyano, halogen, carbalkoxy having 2 to 9 carbon atoms or carboxamido, or $B_2$ is cycloalkyl which has 5 or 6 carbon atoms and is unsubstituted or substituted by methyl or methoxy, or $B_2$ is aralkyl which has 1 to 4 carbon atoms in the alkyl moiety and is unsubstituted or substituted in the aryl moiety by alkyl or alkoxy having 1 to 4 carbon atoms, or $B_2$ is substituted or unsubstituted aryl, $R_4$, $R_5$ and $R_6$ independently of one another are alkyl which has in each case 1 to 8 carbon atoms and is unsubstituted or substituted by methoxy, hydroxyl, cyano, halogen or carboxamido, or are cycloalkyl which has 5 or 6 carbon atoms and is unsubstituted or substituted by methyl or methoxy, or are aralkyl which has 1 to 4 carbon atoms in the alkyl moiety and is unsubstituted or substituted in the aryl moiety by alkyl or alkoxy having in each case 1 to 4 carbon atoms, or are $H\text{-}(OC_2H_4)_{\overline{n}1}$, in which $n_1$ is 1, 2 or 3, $Z_2$ is substituted or unsubstituted phenylene and X and m are as defined above.

The compounds of the formula

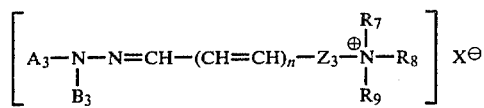

in which $A_3$ is phenyl which is unsubstituted or substituted by alkyl or alkoxy having in each case 1 to 4 carbon atoms, hydroxyl or halogen, it being possible for the phenyl ring to carry 1 or 2 substituents, $B_3$ is hydrogen, alkyl which has 1 to 4 carbon atoms and is unsubstituted or substituted by methoxy, hydroxyl, cyano, chlorine, carbalkoxy having 2 to 9 carbon atoms or carboxamido, or $B_3$ is cyclohexyl which is unsubstituted or substituted by methyl or methoxy, or $B_3$ is aralkyl which has 1 to 4 carbon atoms in the alkyl moiety and is unsubstituted or substituted in the aryl moiety by alkyl or alkoxy having in each case 1 or 2 carbon atoms, or is phenyl which is unsubstituted or substituted by alkoxy having 1 or 2 carbon atoms, $R_7$, $R_8$ and $R_9$ independently of one another are alkyl which has in each case 1 to 4 carbon atoms and is unsubstituted or substituted by methoxy, hydroxyl, cyano, chlorine or carboxamido, or are cyclohexyl which is unsubstituted or substituted by methyl or methoxy, or are aralkyl which has 1 to 4 carbon atoms in the alkyl moiety and is unsubstituted or substituted in the aryl moiety by alkyl or alkoxy having in each case 1 or 2 carbon atoms, or are $H-(OC_2H_4)_{n_2}$, in which $n_2$ is 1 or 2, $Z_3$ is phenylene which is unsubstituted or substituted by alkyl or alkoxy having in each case 1 to 4 carbon atoms, hydroxyl, cyano, nitro or halogen, it being possible for the phenyl ring to contain 1 or 2 of the substituents, and $X^\ominus$ and m are as defined above, are also preferred.

Valuable compounds of the formula (3) are the compounds of the formula

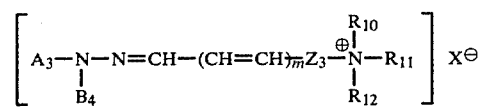

in which $B_4$ is hydrogen, alkyl which has 1 to 4 carbon atoms and is unsubstituted or substituted by hydroxyl, cyano, carbalkoxy having 2 to 9 carbon atoms or carboxamido, or $B_4$ is cyclohexyl, benzyl, phenethyl, or phenyl which is unsubstituted or substituted by methoxy or ethoxy, $R_{10}$, $R_{11}$ and $R_{12}$ independently of one another are alkyl which has in each case 1 to 4 carbon atoms and is unsubstituted or substituted by hydroxyl, or are benzyl, phenethyl or $H-(OC_2H_4)_{n_2}$, in which $n_2$ is as defined above, and $A_3$, $Z_3$, $X^\ominus$ and m are as defined above.

The compounds of the formula

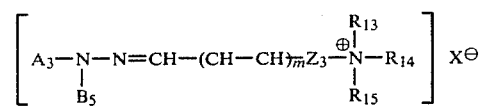

in which $B_5$ is hydrogen, alkyl which has 1 or 2 carbon atoms and is unsubstituted or substituted by hydroxyl, cyano, carbalkoxy having 2 to 5 carbon atoms or carboxamido, or $B_5$ is benzyl or phenyl, $R_{13}$, $R_{14}$ and $R_{15}$ independently of one another are alkyl having in each case 1 or 2 carbon atoms, benzyl or $H-(OC_2H_4)_{n_2}$, in which $n_2$ is as defined above, and $A_3$, $Z_3$, $X^\ominus$ and m are as defined above, and of the formula

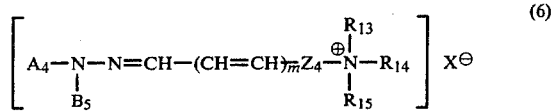

in which $A_4$ is phenyl which is unsubstituted or substituted by alkyl or alkoxy having in each case 1 or 2 carbon atoms or chlorine, it being possible for the phenyl ring to carry 1 or 2 of the substituents, $Z_4$ is 1,4-phenylene which is unsubstituted or substituted by methoxy, hydroxyl or chlorine, it being possible for the phenylene ring to carry 1 or 2 of the substituents, and $B_5$, $R_{13}$, $R_{14}$, $R_{15}$, $X^\ominus$ and m are as defined above, are also of interest.

Particularly valuable compounds of the formula (6) are the compounds of the formula

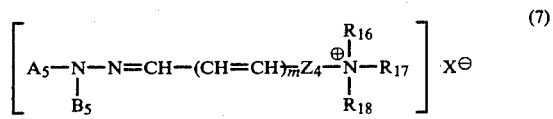

in which $A_5$ is phenyl which is unsubstituted or substituted by methyl, methoxy or chlorine, it being possible for the phenyl ring to carry 1 or 2 of the substituents, $R_{16}$, $R_{17}$ and $R_{18}$ independently of one another are methyl, benzyl or $HO-C_2H_4-$ and $B_5$, $Z_4$, $Z^\ominus$ and m are as defined above.

The compounds of the formula (1) can be prepared by condensing the compound of the formula

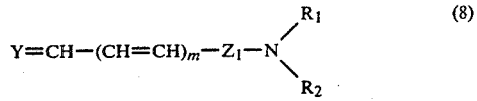

in which Y is oxygen or $=N-D$, in which D is an aromatic radical, and $Z_1$, $R_1$, $R_2$ and m are as defined above, with a hydrazine of the formula

in which $A_1$ and $B_1$ are as defined above, and then quaternising the nitrogen atom adjacent to $Z_1$.

Preferred compounds of the formula (8) are, for example, 4-dimethylaminobenzaldehyde, 4-diethylaminobenzaldehyde and 4-dimethylaminocinnamaldehyde.

Suitable hydrazines of the formula (9) are, for example, N-phenyl-N-methylhydrazine, N-phenyl-N-ethylhydrazine, N-phenyl-N-benzylhydrazine, N-(4-methylphenyl)-N-methylhydrazine, N-(4-methoxyphenyl)-N-methylhydrazine and N-(4-chlorophenyl)-N-methylhydrazine.

In another process, hydrazone derivatives of the formula (1) are prepared by reacting the compound of the formula (8) with a hydrazine of the formula

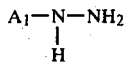

in which $A_1$ is as defined above, and then replacing the hydrogen atom which is geminal relative to $A_1$ by $B_1$ and subsequently quaternising the nitrogen atom adjacent to $Z_1$.

The replacement and quaternisation can be carried out either successively or in one step.

Compounds of the formula (1) can also be prepared directly by reacting the quaternised compound

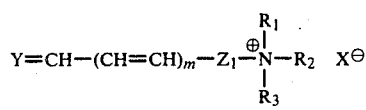

in which Y, $Z_1$, $R_1$, $R_2$, $R_3$, $X^\ominus$ and m are as defined above, with a hydrazine of the formula (9).

The condensation of the compounds (8) and (9), (8) and (10) and (9) and (11) is advantageously carried out in a solvent, preferably in an alcohol, for example methanol or ethanol. Suitable quaternising agents are, for example, dimethyl sulfate, diethyl sulfate, p-toluene-sulfonates, benzyl bromide or methyl iodide. The quaternisation is preferably carried out in a solvent, for example acetone, methyl ethyl ketone, ligroin, chloroform, benzene, toluene or chlorobenzene.

The compounds of formula (1) according to the present invention are water-soluble substances which are firmly bonded by natural or synthetic compounds which have a high molecular weight and contain acid groups, in a similar manner to basic dyes. Suitable natural compounds of high molecular weight are, for example, hydrophilic colloids, for example gelatin or alginates. Suitable synthetic substances of high molecular weight are, for example, homopolymers and copolymers of acrylic acid and methacrylic acid or of acrylonitrile, and also acid esters of polyvinyl alcohol and other polymers containing hydroxyl groups, as well as homopolymers and copolymers of maleic anhydride. The compounds of the formula (1) according to the present invention absorb ultraviolet and visible radiation at wavelengths in the range between about 320 and 450 nm. They are therefore suitable as UV absorbers for all the customary fields of use, for example for protecting dyes from the effect of ultraviolet light or for protecting human skin from the effect of sunlight. As a result of their cationic nature, they are particularly suitable in all cases where the substance to be protected or, for example, a binder surrounding the substance to be protected has an acid nature and is therefore capable of bonding the UV absorbers according to the present invention.

An important application for which the compounds of the formula (1) according to the present invention are particularly suitable is the "colouring" of acid photopolymers with UV-absorbing substances. Photopolymers are frequently used as masks for the production of copies. Photopolymers which can be used for such purposes must be opaque to photochemically active radiation, preferably in the ultraviolet to blue region.

Suitable photopolymers are, for example, the polymers which contain dimethylmaleimide groups and, in the polymer chain, free acid groups, for example from acrylic acid or methacrylic acid molecules incorporated in the chain, and which are prepared in accordance with the method of European Published Patent Application No. 21019. According to the said patent application, such photopolymers can be coloured with cationic dyes after irradiation and at the same time as or after, development with alkaline aqueous solutions.

Instead of the customary cationic dyes, it is thus also possible for cationic UV absorbers to be successfully used for the same purpose. This treatment renders the photopolymer opaque to ultraviolet radiation at the exposed points after development and colouring, and the photopolymer is thus suitable for the production of copies or as a mask, for example for the production of printed circuits, or semiconductor elements with integrated circuits, where photo-layers which are sensitive in the UV range are preferably used for the production of these products. For this purpose, the image areas containing UV absorbers according to the present invention can also be made visible to the eye by further dyes which absorb in the visible region of the spectrum.

The examples which follow are intended to illustrate the preparation and use of the cationic UV absorbers according to the invention.

Parts and percentages are by weight.

PREPARATION EXAMPLES

Example 1

61 parts of 4-dimethylaminobenzaldehyde are dissolved in 450 parts of ethyl alcohol and 45 parts of acetic acid at 40° C. 50 parts of N-methyl-N-phenylhydrazine, dissolved in 250 parts of ethanol and 250 parts of water, are slowly added dropwise, with stirring. The compound of the formula

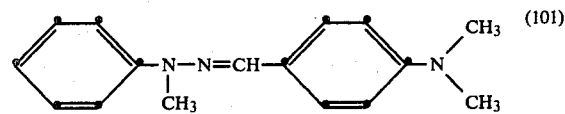

of melting point 144°–146° C. is obtained in quantitative yield.

| | Analysis: | |
|---|---|---|
| | % calculated | % found |
| C | 75.86 | 75.67 |
| H | 7.56 | 7.53 |
| N | 16.59 | 16.75 |

Subsequent quaternisation is carried out by heating a suspension of 10 parts of the compound (101) in 40 parts of methyl ethyl ketone to 70° C. and then adding 5 parts of dimethyl sulfate. After about 10 minutes, the compound of the formula

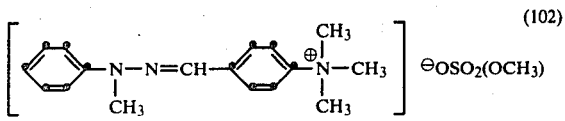

crystallises out.

The melting point is 144°–150° C.; $\lambda$ max=355 nm and $\epsilon$=25,000.

| Analysis: | |
|---|---|
| % calculated | % found |
| C | 56.97 | 56.70 |
| H | 6.64 | 6.60 |
| N | 11.07 | 11.23 |

The procedure described in the above example is repeated using N-methyl-N-(4-chlorophenyl)-hydrazine instead of N-methyl-N-phenylhydrazine. The correspondhydrazone of 4-dimethylaminobenzaldehyde, of the formula

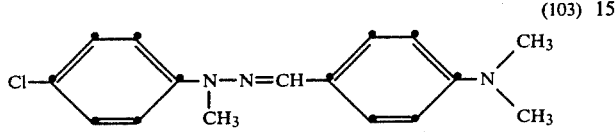
(103)

is obtained. The melting point is 161°–162° C., λ max=365 nm and ε=34,000.

| Analysis: | |
|---|---|
| % calculated | % found |
| C | 66.78 | 66.95 |
| H | 6.31 | 6.25 |
| N | 14.61 | 14.70 |

This compound is reacted as described above to give the compound of the formula

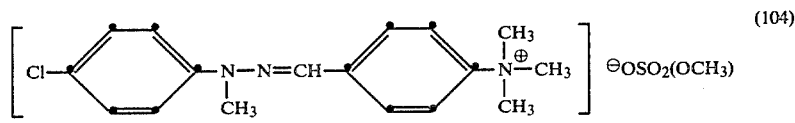
(104)

The melting point is 171°–172° C., λ max=350 nm and ε=28,000.

Example 2

The compound of the formula

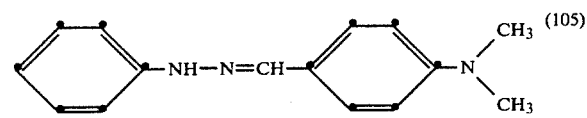
(105)

is prepared according to Example 1 by reacting 4-dimethylaminobenzaldehyde with phenylhydrazine.

The melting point is 144°–147.5° C., λ max=360 nm and ε=35,000.

| Analysis: | |
|---|---|
| % calculated | % found |
| C | 55.87 | 55.88 |
| H | 6.34 | 6.38 |
| N | 11.49 | 11.48 |

20 parts of the compound of the formula (105) are dissolved in 80 parts of methylene chloride. 4.8 parts of acrylonitrile, 1 part of tetraethylammonium bromide and 3.4 parts of sodium hydroxide, dissolved in 3.4 parts of water, are added successively. After about 20 minutes, the aqueous phase is separated off. The organic phase is neutralised, dried and concentrated. 24 parts of the compound of the formula

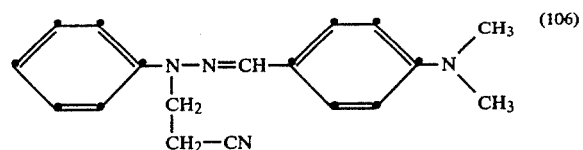
(106)

are obtained. The melting point is 130°–131° C., λ max=355 nm and ε=24,000.

| Analysis: | |
|---|---|
| % calculated | % found |
| C | 73.95 | 74.09 |
| H | 6.90 | 6.88 |
| N | 19.17 | 19.21 |

24 parts of the compound of the formula (106) are dissolved in 85 parts of methyl ethyl ketone, and, after adding 11 parts of dimethyl sulfate, the mixture is heated at 70° C. for 4 hours. 34 parts of the quaternised compound of the formula

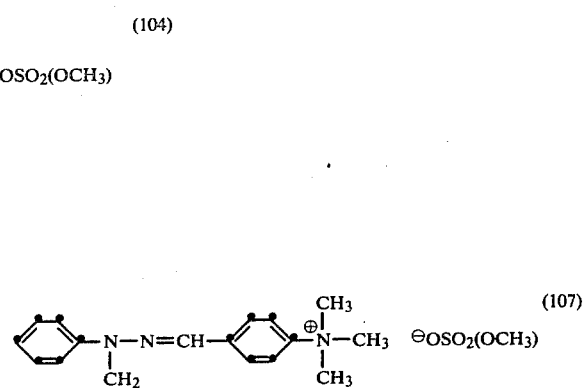
(107)

are obtained. The melting point is 131°–132° C., λ max=340 nm and ε=20,000.

4-Dimethylaminobenzaldehyde and 4-dimethylaminocinnamaldehyde can be reacted with substituted phenylhydrazines in an analogous manner to give the corresponding hydrazones of the formula

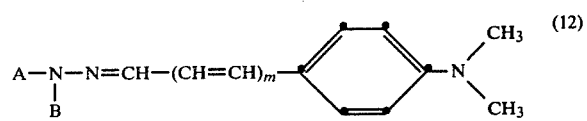
(12)

Examples of these products are summarised in Table 1.

TABLE 1

$$A-\underset{\underset{B}{|}}{N}-N=CH-(CH=CH)_m-\text{[phenyl]}-N(CH_3)_2 \quad (12)$$

| No. | A | B | m | m.p. (°C.) | ε | λmax(nm) | NMR data |
|---|---|---|---|---|---|---|---|
| 108 | CH₃—[phenyl]— | CH₃ | 0 | — | 36,000 | 357 | Singlet: 2.3 ppm (—[phenyl]—CH₃); 2.9 ppm (—N(CH₃)₂); 3.3 ppm (—N(CH₃)—) |
| 109 | CH₃O—[phenyl]— | CH₃ | 0 | 162–164 | 30,000 | 358 | Singlet: 2.9 ppm (—N(CH₃)₂); 3.3 ppm (—N(CH₃)—); 3.7 ppm (—O—CH₃); 6.6–7.6 ppm (9 Protons) |
| 110 | [phenyl]— | CH₃ | 1 | 168–170 | — | — | Singlet: 2.9 ppm (—N(CH₃)₂); 3.25 ppm (N—CH₃); 6.7–7.5 ppm (12 Protons) |

The compounds of the formulae (108), (109) and (110) are reacted as described to give the corresponding quaternised compounds of the formula (13). These products are listed in Table 2.

TABLE 2

$$\left[A-\underset{\underset{B}{|}}{N}-N=CH-(CH=CH)_m-\text{[phenyl]}-\overset{\oplus}{N}(CH_3)_3\right] \ominus OSO_2(OCH_3) \quad (13)$$

| No. | A | B | m | Melting point (°C.) | ε | λmax(nm) | Analysis data and NMR data |
|---|---|---|---|---|---|---|---|
| 111 | CH₃O—[phenyl]— | CH₃ | 0 | 176–177 | 28,000 | 348 | Singlet: 3.15 ppm (N—CH₃); 3.70 ppm N⊕(CH₃)₃; 3.78 ppm —O—CH₃; 3.95 ppm ⊖OSO₂(OCH₃) |
| 112 | CH₃—[phenyl]— | CH₃ | 0 | 192–194 | 26,000 | 349 | % calculated: C 57.99, H 6.91, N 10.68; % found: C 57.90, H 7.05, N 10.62 |
| 113 | [phenyl]— | CH₃ | 1 | 187–190 | 30,000 | 365 | Singlet: 3.3 ppm (N—CH₃); 3.4 ppm ⊖OSO₂(OCH₃); 3.6 ppm ⊕N—(CH₃)₃; 6.1–7.2 ppm (12 Protons) |

TABLE 2-continued $$\left[ A-\underset{B}{N}-N=CH-(CH=CH)_m-\underset{}{\bigcirc}-\overset{\oplus}{\underset{CH_3}{N}}\underset{CH_3}{-CH_3} \right] \ominus OSO_2(OCH_3) \quad (13)$$

| No. | A | B | m | Melting point (°C.) | ε | λmax(nm) | Analysis data and NMR data | | | |
|-----|---|---|---|---------------------|---|----------|---|---|---|---|
| | | | | | | | | C | H | N |
| 114 | 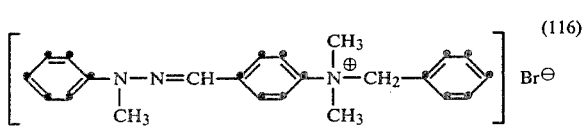 | H | 0 | 197–198 | 20,000 | 341 | % calculated | 55.87 | 6.34 | 11.49 |
| | | | | | | | % found | 55.76 | 6.38 | 11.45 |
| 115 | | H | 1 | 205–209 | 25,000 | 365 | Singlet: 3.16 ppm (⊕N—CH₃) 6.7–7.9 ppm 3.9 ppm ⊖OSO₂(OCH₃), aromatics | | | |

Example 4

10 parts of the compound (101) are suspended in 50 parts of acetonitrile. The suspension is warmed to 70° C. and 6.3 parts of benzyl bromide are added, with stirring. The mixture is left at 70° C. for 3 hours. It is then allowed to cool to room temperature. The precipitate formed is filtered off, washed with acetonitrile and dried. 12 parts of the compound $$\left[ \bigcirc-\underset{CH_3}{N}-N=CH-\bigcirc-\overset{\oplus}{\underset{CH_3}{N}}-CH_2-\bigcirc \right] Br^{\ominus} \quad (116)$$

are obtained. The melting point of this compound is 119°–122° C., λ max=345 nm and ε=26,000.

NMR data: singlet: 3.7 ppm —N⁺(CH₃)₃; 5.3 ppm methylene protons=N⁺—CH₂—C₆H₅; 7.1–7.9 ppm aromatics and —CH=N—.

USE EXAMPLES

Example 5

A 2μ thick light-sensitive layer consisting of a polymer of 20% of methacrylic acid and 80% of N-(2-methacrylyloxyethyl)-dimethylmaleimide, which has first been sensitised with a thioxanthone compound, is applied to a polyester carrier.

A strip of the coated material is exposed, image-wise, behind a transparent original and is then developed by immersion in a 2% solution of the compound of the formula (102) in an 0.25 molar aqueous solution of trisodium phosphate. The strip is then washed in water for 30 seconds and subsequently dried.

A negative image which absorbs UV light and has an optical density, measured at λ=355 nm of greater than 5.0 after a development time of 20 seconds is obtained.

Example 6

A 2μ thick layer of a photocrosslinking polymer which has been obtained by copolymerisation of 20% of methacrylic acid, 20% of ethyl acrylate and 60% of N-(2-methacrylyloxyethyl)-dimethylmaleimide (intrinsic viscosity: 0.24) and has been sensitised with a thioxanthone compound is applied to a polyester carrier.

As in Example 5, a strip of this material is exposed, imagewise, behind a transparent original and is then immersed for 20 seconds in a solution which is prepared as follows: 22 g of the compound of the formula (102), 25 g of the dye CI 48055 and 22 g of the azo dye of the formula

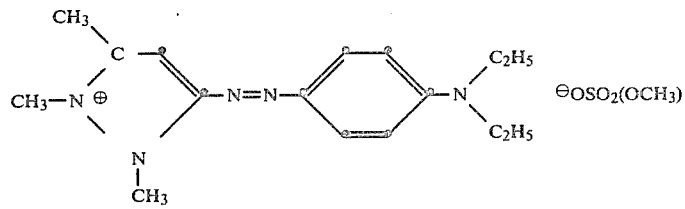

are dissolved in 2,000 g of a 0.25 molar solution of trisodium phosphate. The solution is adjusted to a pH value of 13.0 by the addition of 30% sodium hydroxide solution.

The strip is then washed with wter and dried. In the image areas, the material has an optical density of at least 3.0 over the entire spectral range between 350 and 500 nm.

Example 7

A strip of the material used in Example 5 is exposed in the manner described above and is then developed by immersion in a 5% solution of sodium carbonate and subsequently washed with water. The strip is then coloured by immersion in a solution of 1.5% by weight of the compound of the formula (102), 4.0% by weight of the dye CI 48055, 0.75% by weight of the dye CI 48035, 0.75% by weight of the dye CI 11055 (s) and 0.25% by weight of sodium carbonate for 20 seconds, and is subsequently washed out with water. After the strip has been dried, the optical density in the image areas is at least 3.0 in the entire spectral range between 350 and 500 nm.

Example 8

A 3 μm thick layer of a photocrosslinkable copolymer which has been prepared by copolymerisation of 15% of methacrylic acid, 25% of ethyl acrylate and 60% of N-(2-methacrylyloxyethyl)-dimethylmaleimide (intrinsic viscosity=0.29 dl/g; 0.5% in methyl ethyl ketone/methylcellosolve 1:1; 25° C.) and has been sensitised with 8% (based on the solids content) of a thioxanthone compound, is applied to a 0.1 mm thick polyester carrier.

Four samples of this material are exposed and are immersed for 20 seconds in an agitated 5% aqueous sodium bicarbonate solution, which has been adjusted to a pH value of 9.7 with 30% sodium hydroxide solution and is at a temperature of 35° C. The samples are then rinsed in deionised water at room temperature for 20 seconds. Each sample is dyed for immersion in a different dye solution (A, B, C, or D) for 20 seconds. The temperature of each dye solution is 20° C. The dye solutions are prepared as follows:

2 g of a cationic UV absorber are dissolved in 100 ml of a buffer solution, which has been prepared by dissolving 10 g of KH$_2$PO$_4$ in 2,490 g of deionised water. The pH value of this solution has been adjusted to 6.0 or 7.0 with the aid of 30% aqueous potassium hydroxide solution. The compounds of the formulae (102), (113) and (114) and the compound of the formula

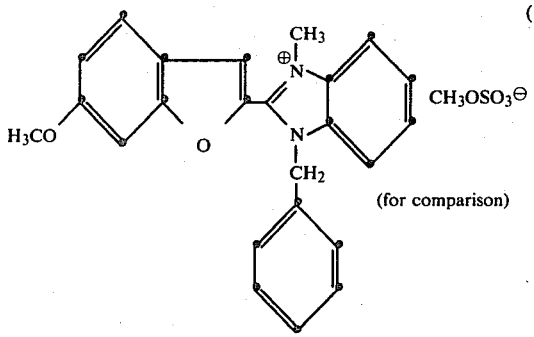

(117)

(for comparison)

are employed as the cationic UV absorbers.

Compound (117) is a commercially available fluorescent brightener.

The dyed samples are washed in water for 30 seconds and dried. The optical density of the samples is determined using a UV spectrophotometer. The results are summarised in Table 3.

TABLE 3

| Dye solution | Optical density at pH 6 (at λ$_{max}$) | Optical density at pH 7 | Optical densities ≧3.0 at pH 7 over |
|---|---|---|---|
| A (containing compound (102)) | >5.0 (350 nm) | >5.0 | 315–385 nm |
| B (containing compound (113)) | >5.0 (375 nm) | >5.0 | 340–410 nm |
| C (containing compound (114)) | >5.0 (360 nm) | >5.0 | 320–400 nm |
| D (containing compound (117)) for comparison | >3.8 (355 nm) | 4.2 | 330–380 nm |

From the table, it can be seen that, both on the basis of their optical density and of the effective spectral range, the compounds of the formulae (102), (113) and (114) according to the present invention have considerably better dyeing properties than the comparison compound of the formula (117).

What is claimed is:

1. A hydrazone derivative of the formula

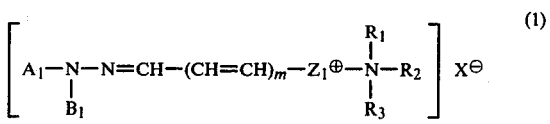

(1)

in which A$_1$ is phenyl or naphthyl, unsubstituted or substituted by alkyl or alkoxy with 1 to 4 carbon atoms, hydroxyl or halogen; B$_1$ is hydrogen, alkyl having 1 to 8 carbon atoms and being unsubstituted or substituted by methoxy, hydroxyl, cyano, halogen, carboxamido or carbalkoxy having 2 to 9 carbon atoms; cycloalkyl having 5 or 6 ring carbon atoms and being unsubstituted or substituted by alkyl or alkoxy of 1 or 2 carbon atoms; phenyl- or naphthyl-alkyl having 1 to 4 carbon atoms in the alkyl moiety and being unsubstituted or substituted in the phenyl or naphthyl moiety by alkyl or alkoxy of 1 to 4 carbon atoms; or phenyl or naphthyl being unsubstituted or substituted by alkoxy of 1 to 4 carbon atoms; R$_1$, R$_2$ and R$_3$ independently of one another are alkyl of 1 to 8 carbon atoms being unsubstituted or substituted by methoxy, hydroxyl, cyano, halogen or carboxamide; cycloalkyl having 5 to 6 ring carbon atoms and being unsubstituted or substituted by methyl or methoxy; or phenylalkyl having 1 to 4 carbon atoms in the alkyl moiety and being unsubstituted or substituted in the phenyl moiety by alkyl or alkoxy of 1 to 4 carbon atoms; polyoxaalkylene of formula H—(OC$_2$H$_4$)$_{n_1}$, wherein n$_1$ is 2 or 3; Z$_1$ is phenylene or naphthylene being unsubstituted or substituted by hydroxyl, nitro, cyano, halogen or alkyl or alkoxy of 1 to 4 carbon atoms, X$^\ominus$ is an anion and m is 0, 1, 2 or 3.

2. A compound according to claim 1, of the formula

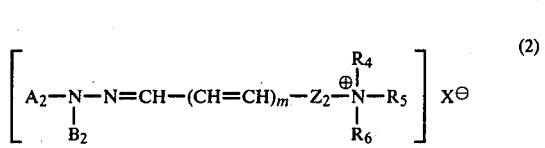

(2)

in which A$_2$ is phenyl substituted by alkyl or alkoxy of 1 to 4 carbon atoms, hydroxyl or halogen or unsubstituted; B$_2$ is hydrogen, alkyl which has 1 to 8 carbon atoms and is unsubstituted or substituted by methoxy, hydroxyl, cyano, halogen, carbalkoxy having 2 to 9 carbon atoms or carboxamido, or B$_2$ is cycloalkyl which has 5 or 6 carbon atoms and is unsubstituted or substituted by methyl or methoxy, or B$_2$ is phenyl- or naphthylalkyl which has 1 to 4 carbon atoms in the alkyl moiety and is unsubstituted or substituted in the phenyl or naphthyl moiety by alkyl or alkoxy having 1 to 4 carbon atoms, or B$_2$ is phenyl or naphthyl, unsubstituted or substituted by alkoxy of 1 to 4 carbon atoms, R$_4$, R$_5$ and R$_6$ independently of one another are alkyl which has in each case 1 to 8 carbon atoms and is unsubstituted or substituted by methoxy, hydroxyl, cyano, halogen or carboxamido, or are cycloalkyl which has 5 or 6 carbon atoms and is unsubstituted or substituted by methyl or methoxy, or are phenylalkyl which has 1 to 4 carbon atoms in the alkyl moiety and is unsubstituted or substituted in the phenyl moiety by alkyl or alkoxy having in each case 1 to 4 carbon atoms, or are H$\leftarrow$OC$_2$H$_4$)$_{n1}$, in which $n_1$ is 2 or 3, $Z_2$ is phenylene unsubstituted or substituted by hydroxyl, nitro cyano, halogen or alkyl or alkoxy of 1 to 4 carbon atoms and X$^\ominus$ and m are as defined in claim 1.

3. A compound according to claim 2, of the formula

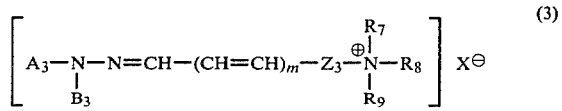

in which A$_3$ is phenyl which is unsubstituted or substituted by alkyl or alkoxy having in each case 1 to 4 carbon atoms, hydroxyl or halogen, it being possible for the phenyl ring to carry 1 or 2 substituents, B$_3$ is hydrogen, alkyl which has 1 to 4 carbon atoms and is unsubstituted or substituted by methoxy, hydroxyl, cyano, chlorine, carbalkoxy having 2 to 9 carbon atoms or carboxamido, or B$_3$ is cyclohexyl which is unsubstituted or substituted by methyl or methoxy, or B$_3$ is phenyl- or naphthylalkyl which has 1 to 4 carbon atoms in the alkyl moiety and is unsubstituted or substituted in the phenyl or naphthyl moiety by alkyl or alkoxy having in each case 1 or 2 carbon atoms, or is phenyl which is unsubstituted or substituted by alkoxy having 1 to 2 carbon atoms, R$_7$, R$_8$ and R$_9$ independently of one another are alkyl which has in each case 1 to 4 carbon atoms and is unsubstituted or substituted by methoxy, hydroxyl, cyano, chlorine or carboxamido, or are cyclohexyl which is unsubstituted or substituted by methyl or methoxy, or are phenylalkyl which has 1 to 4 carbon atoms in the alkyl moiety and is unsubstituted or substituted in the phenyl moiety by alkyl or alkoxy having in each case 1 or 2 carbon atoms, or are H$\leftarrow$OC$_2$H$_4$)$_{n2}$, in which $n_2$ is 2, Z$_3$ is is phenylene which is unsubstituted or substituted by alkyl or alkoxy having in each case 1 to 4 carbon atoms, hydroxyl, cyano, nitro or halogen, it being possible for the phenyl ring to contain 1 or 2 of the substituents, and X$^\ominus$ and m are as defined in claim 2.

4. A compound according to claim 3, of the formula

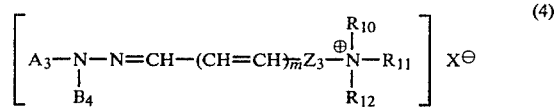

in which B$_4$ is hydrogen, alkyl which has 1 to 4 carbon atoms and is unsubstituted or substituted by hydroxyl, cyano, carbalkoxy having 2 to 9 carbon atoms or carboxamido, or B$_4$ is benzyl, phenethyl, or phenyl which is unsubstituted or substituted by methoxy or ethoxy; or cyclohexyl; R$_{10}$, R$_{11}$ and R$_{12}$ independently of one another are alkyl which has in each case 1 to 4 carbon atoms and is unsubstituted or substituted by hydroxyl, or are benzyl, phenethyl or H$\leftarrow$OC$_2$H$_4$)$_{n2}$, in which $n_2$ is 2 and A$_3$, Z$_3$, X$^\ominus$ and m are as defined in claim 3.

5. A compound according to claim 4, of the formula

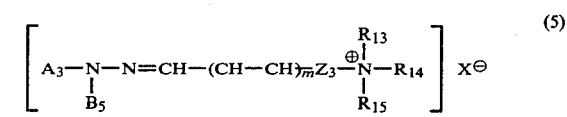

in which B$_5$ is hydrogen, alkyl which has 1 or 2 carbon atoms and is unsubstituted or substituted by hydroxyl, cyano, carbalkoxy having 2 to 5 carbon atoms or carboxamido, or B$_5$ is benzyl or phenyl, R$_{13}$, R$_{14}$ and R$_{15}$ independently of one another are alkyl having in each case 1 or 2 carbon atoms, benzyl or H—OC$_2$H$_4$)$_{n2}$, in which $n_2$ is 2, and A$_3$, Z$_3$, X$^\ominus$ and m are as defined in claim 4.

6. A compound according to claim 5, of the formula

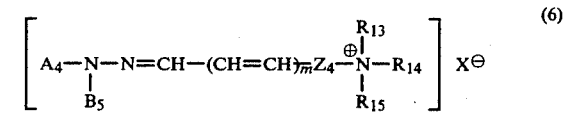

in which A$_4$ is phenyl, which is unsubstituted or substituted by alkyl or alkoxy having in each case 1 or 2 carbon atoms or chlorine, it being possible for the phenyl ring to carry 1 or 2 of the substituents, Z$_4$ is 1,4-phenylene which is unsubstituted or substituted by methoxy, hydroxyl or chlorine, it being possible for the phenylene ring to carry 1 or 2 of the substituents, and B$_5$, R$_{13}$, R$_{14}$, R$_{15}$, X$^\ominus$ and m are as defined in claim 5.

7. A compound according to claim 6, of the formula

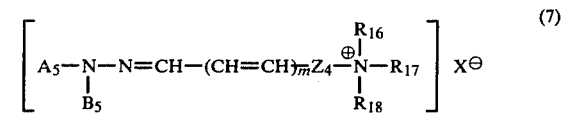

in which A$_5$ is phenyl which is unsubstituted or substituted by methyl, methoxy or chlorine, it being possible for the phenyl ring to carry 1 or 2 of the substituents, R$_{16}$, R$_{17}$ and R$_{18}$ independently of one another are methyl, benzyl or HO—C$_2$H$_4$—$_{n2}$ and B$_5$, Z$_4$, X$^\ominus$ and m are as defined in claim 6.

* * * * *